US011276496B2

(12) United States Patent
Kenig et al.

(10) Patent No.: US 11,276,496 B2
(45) Date of Patent: Mar. 15, 2022

(54) METHOD AND SYSTEMS FOR A HEALTHCARE PROVIDER ASSISTANCE SYSTEM

(71) Applicant: General Electric Company, Schenectady, NY (US)

(72) Inventors: Tal Kenig, Seattle, WA (US); Paul Mullen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 157 days.

(21) Appl. No.: 16/198,710

(22) Filed: Nov. 21, 2018

(65) Prior Publication Data

US 2020/0160995 A1    May 21, 2020

(51) Int. Cl.
*G06Q 10/00* (2012.01)
*G16H 50/20* (2018.01)
*G16H 10/60* (2018.01)

(52) U.S. Cl.
CPC ............ *G16H 50/20* (2018.01); *G16H 10/60* (2018.01)

(58) Field of Classification Search
CPC ........ G16H 10/60; G16H 50/20; G16H 15/00; G16H 40/20; G16H 50/70; G16H 80/00; G16H 10/20; G16H 40/63; G16H 10/40; G16H 20/40; G16H 50/30; G16H 20/10; G16H 70/60; G16H 20/70; G16H 30/40; G16H 50/50; G16H 70/20; G16H 30/20; G06Q 50/24; G06Q 10/10; G06F 19/328; G06F 19/3418; G06F 19/3481; G06F 3/0482; G06F 19/321; G06F 3/04842; G06F 19/00
See application file for complete search history.

(56) References Cited

U.S. PATENT DOCUMENTS

| 2004/0078231 | A1 | 4/2004 | Wilkes et al. |
| 2004/0122701 | A1 | 6/2004 | Dahlin et al. |
| 2008/0091464 | A1* | 4/2008 | Lipscher ................ G06Q 40/08 705/2 |

(Continued)

OTHER PUBLICATIONS

PCT Application No. PCT/US2019/062330 filed Nov. 20, 2019; International Search Report/Written Opinion issued Apr. 22, 2020; 11 pages.

*Primary Examiner* — Maroun P Kanaan

(74) *Attorney, Agent, or Firm* — McCoy Russell LLP

(57) ABSTRACT

Various methods and systems are provided for a healthcare provider assistance system. In one example, a system includes a machine-human interface and a computing device operably coupled to the machine-human interface and configured to execute instructions stored in memory to: execute a plurality of different algorithms where inputs to each of the plurality of different algorithms include current and past data representing a health and current condition of a patient, where each of the plurality of different algorithms uses the same data, or a subset of the same data, for the inputs; output, to the machine-human interface, a list of a first number of possible diagnoses of the patient based on outputs of the executed plurality of different algorithms; and present, via the machine-human interface, suggested next actions to narrow down the first number of possible diagnoses, the suggested next actions determined based on the outputs of the executed plurality of different algorithms.

20 Claims, 9 Drawing Sheets

(56) References Cited

U.S. PATENT DOCUMENTS

| | | |
|---|---|---|
| 2010/0324936 A1 | 12/2010 | Vishnubhatla et al. |
| 2015/0012297 A1 | 1/2015 | Ash |
| 2017/0055863 A1 | 3/2017 | Baumann |
| 2018/0096740 A1 | 4/2018 | Moturu |
| 2019/0198172 A1* | 6/2019 | Nelson, Jr. ............ G16H 40/63 |

* cited by examiner

METHOD AND SYSTEMS FOR A HEALTHCARE PROVIDER ASSISTANCE SYSTEM

FIELD

Embodiments of the subject matter disclosed herein relate to healthcare diagnosis of a patient, and in particular to providing assistance in diagnosing the patient using an electronic interface.

BACKGROUND

Health care providers (e.g., physicians, nurse practitioners, and physician's assistants) utilize a thought processes, referred to as differential diagnosis, in diagnosing a patient. Differential diagnosis involves determining multiple possible diagnoses of the illness of the patient based on the available patient health data and symptoms of the patient. The physician then narrows down the differential diagnosis, by performing additional diagnostic tests or assessing additional health data of the patient until he/she is confident that he/she has identified the correct diagnosis. Gathering the health data of the patient for differential diagnosis may involve the care provider searching for medical information regarding the patient in multiple, different hospital (or clinic) information systems (e.g., referred to as "Healthcare Information Technology (HCIT) systems"). This process may be time consuming and error prone, especially when the patient has an extensive medical history. Additionally, the care giver may need to consult available medical standards and guidelines, or recall these from memory, when performing the differential diagnosis and deciding how to treat the patient. This may also be time consuming and/or result in the care provider missing a possible diagnosis.

BRIEF DESCRIPTION

In one embodiment, a system comprises a machine-human interface and a computing device operably coupled (e.g., via a wired or wireless connection, such as via the internet, Bluetooth, the cloud, and the like) to the machine-human interface and configured to execute instructions stored in memory to: execute a plurality of different algorithms where inputs to each of the plurality of different algorithms include current and past data representing a health and current condition of a patient, where each of the plurality of different algorithms uses the same data, or a subset of the same data, for the inputs; output, to the machine-human interface, a list of a first number of possible diagnoses of the patient (e.g., the illness or condition of the patient) based on outputs of the executed plurality of different algorithms; and present, via the machine-human interface, suggested next actions to narrow down the first number of possible diagnoses, the suggested next actions determined based on the outputs of the executed plurality of different algorithms.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
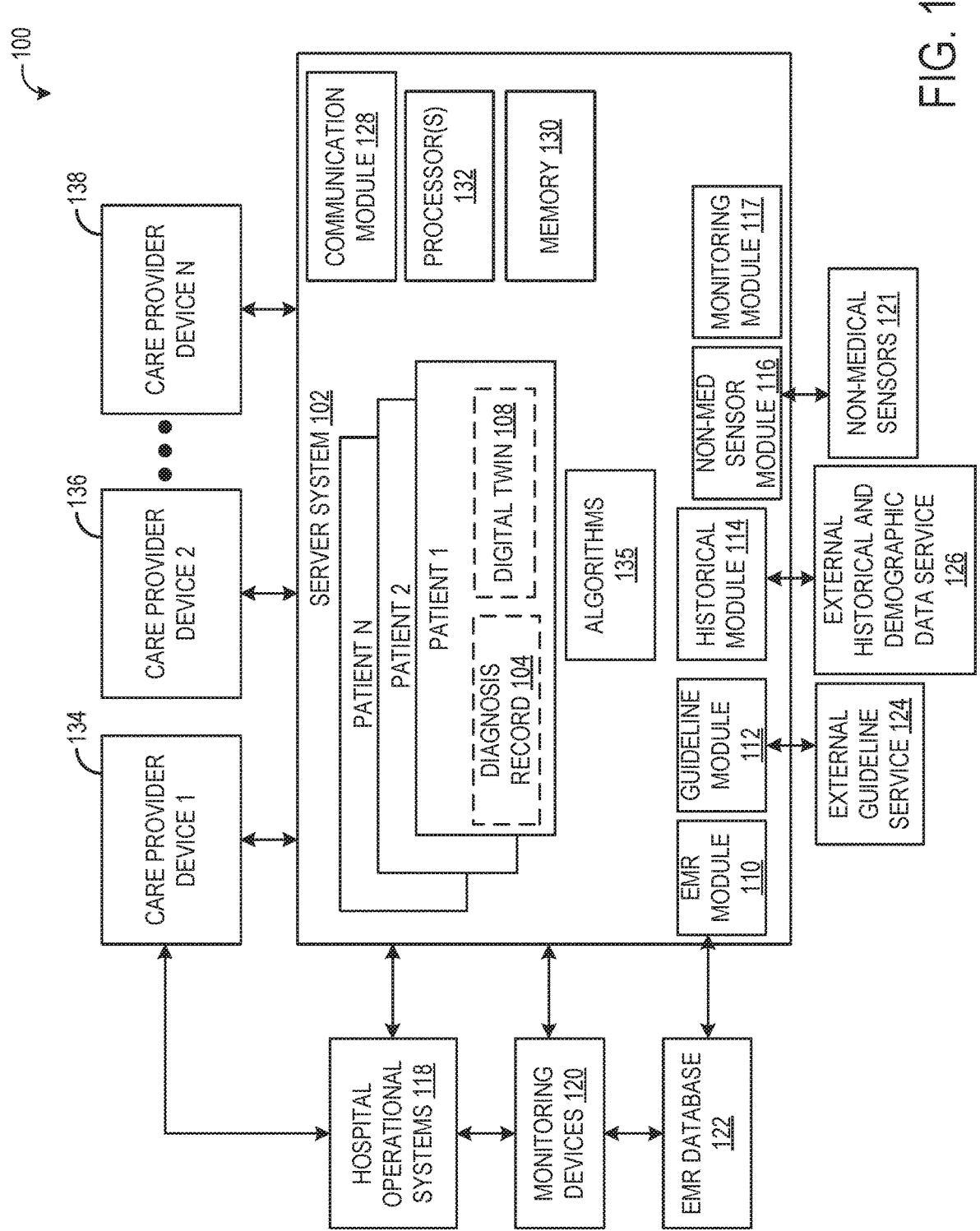
FIG. 1 schematically shows an example healthcare provider assistance system.
Figure 2:
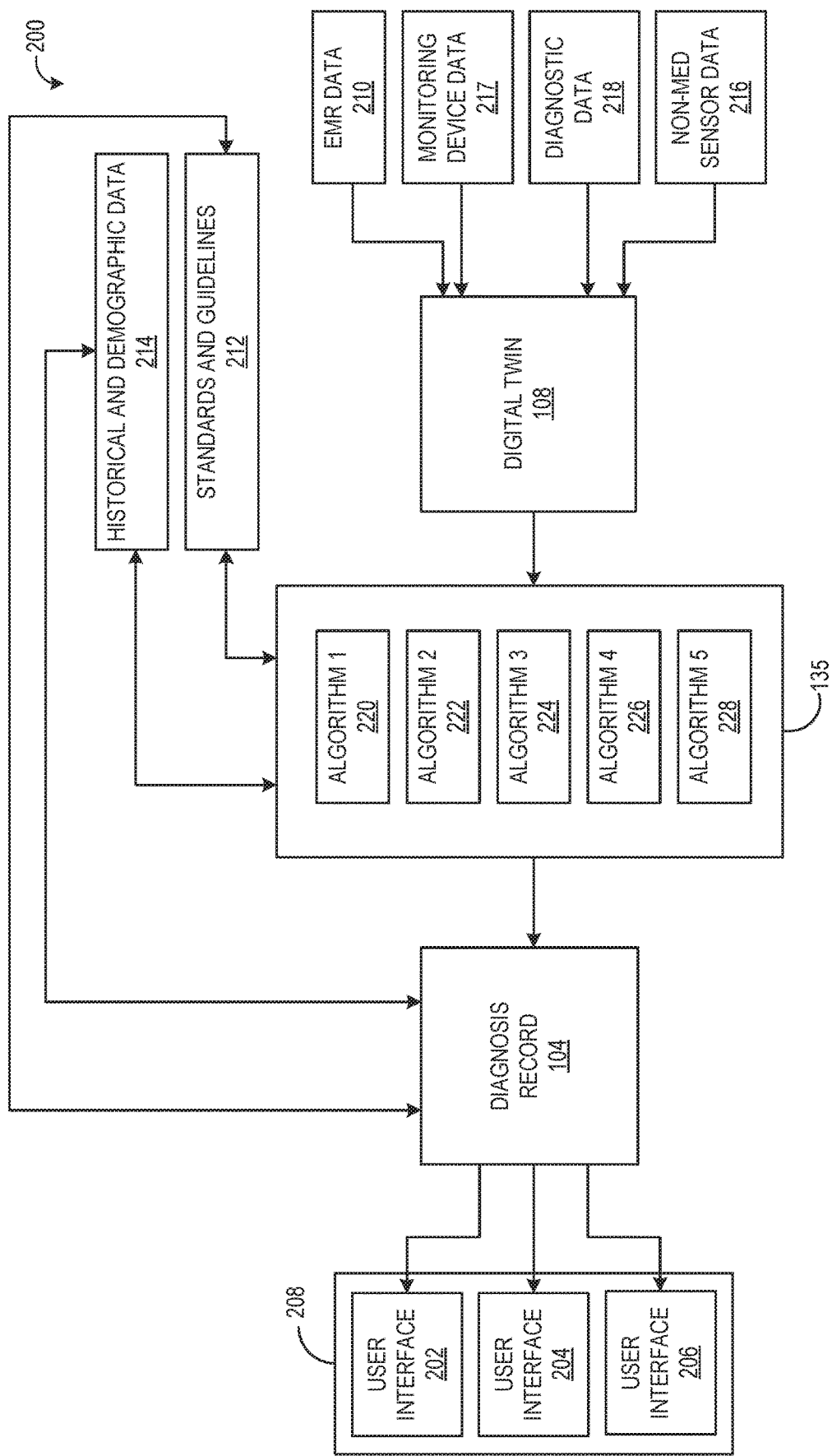
FIG. 2 shows an example schematic of an implementation of the healthcare provider assistance system of FIG. 1.

The following description relates to various embodiments of a healthcare provider assistance system that compiles patient health data from a plurality of sources and offers guidance to a healthcare provider, based on outputs of one or a plurality of algorithms run on the compiled data, in diagnosing and caring for the patient. An example healthcare provider assistance system, including a server system in electronic communication with a care provider device and multiple external services, databases, and monitoring devices is shown in FIG. 1. The server system may employ one or more processor(s) and/or modules to generate a digital representation of health of the patient by compiling and integrating multiple sources of patient health data (including data obtained in real-time and past patient data). In some embodiments, the digital representation of health of the patient may be raw patient health data. In other embodiments, the digital representation of health of the patient may be raw patient health data that has been compiled and manipulated to be more useful as inputs to the algorithms discussed herein. A single and/or a plurality of algorithms stored and executed at the server system may be run on the digital representation of health of the patient (as the input to each algorithm) in order to perform a virtual differential diagnosis on the patient. Outputs of the single and/or plurality of algorithms may be used to form a diagnosis record of the patient which may be presented in various user interfaces, which may include various machine-human interfaces such as a display, audio interface, or the like, to the healthcare provider, as shown in FIG. 2. The diagnosis record may include healthcare insights about the patient, such as current possible diagnoses, future possible diagnoses, and the like. Example user interface displays displayed via a healthcare provider display device are shown at FIGS. 3-8. In one example, a user interface display may include a visualization of a list of possible diagnoses, as determined from outputs of the plurality of algorithms. In some example, each possible diagnosis in the list may have an associated, estimated probability which may also be presented to the user. The user interface display may also present a list of next actions to perform to narrow down the list of possible diagnoses. The user interface may also provide, for each diagnosis, the data elements contributing for the said diagnosis. In this way, the healthcare provider assistance system may suggest a differential diagnosis of the patient condition using patient data compiled from a plurality of different sources and present the differential diagnosis, patient health data, and suggested actions to the healthcare provider in and organized and efficient format. As a result, the healthcare provider may be able to make a more accurate diagnosis while saving time and effort that may be focused toward higher level tasks.

FIG. 1 schematically shows an example healthcare provider assistance system 100 that may be implemented in a medical facility such as a hospital, office, clinic, or remote location of a healthcare provider. Healthcare provider assistance system 100 may include a server system 102. Server system 102 may include resources (e.g., memory 130, processor(s) 132) that may be allocated to store and execute a diagnosis record (which may include one or more diagnosis records including outputs or results of a plurality of algorithms, as explained further below) and a digital twin for each of a plurality of patients. For example, as shown in FIG. 1, a diagnosis record 104 and digital twin 108 are stored on server system 102 for a first patient (patient 1). A plurality of additional diagnosis records and digital twins may be stored on server system 102, each corresponding to a respective patient (patient 2 up to patient N).

The patient medical information, including medical history, current state, vital signs, and other information, as explained further herein, may be entered to the digital twin 108, which may be used as the basis of caregiver's situational awareness, clinical context, and medical history of the patient to facilitate predicted patient states, procurement of relevant treatment guidelines, patient state diagnoses, alternate diagnoses or future predictions of patient diagnoses, etc. As explained further below, the digital twin 108 may be used as an input into a plurality of algorithms configured to facilitate diagnosis of the patient. The plurality of algorithms may predict a health state of the patient, predict a certain diagnosis based on the digital twin, and the like. The diagnosis record 104 may include patient diagnosis data and health status data obtained (e.g., generated or compiled) from outputs of a plurality of algorithms.

As used herein, "diagnosis" may refer to a current or future predicted state of the patient. For example, the diagnosis record 104 may present a list of current, possible diagnoses of the state of the patient, or a trend toward future diagnoses or a future (e.g., change in) state of the patient. As one example, the system described herein may present information to a healthcare provider indicating how long a patient has until reaching certain state or condition (e.g., septic shock), if their current health status continues. In this way, the diagnosis record described herein may provide actionable information, categorization, grouping, classifying, or identifying salient elements about the current state and/or predictions about the future state of a patient that are useful for making care decisions.

The diagnosis record 104, which may include one or more different types of diagnosis reports, may be presented via one or more suitable machine-human interface devices, such as a display and/or audio device, which may be associated with a respective care provider device and/or medical facility administration device. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), audio interface, and/or other subsystems and may be in the form of a desktop computing device, a laptop computing device, a tablet, a smart phone, a smart watch, a smart speaker, wearable goggles, another type of audio device (such as a listening device in a form of an ear piece), or other such device. Each care provider device may be adapted to send and receive encrypted data, display medical information, including medical and non-medical images in a suitable format such as digital imaging and communications in medicine (DICOM) or other standards. The care provider devices may be located locally at the medical facility (such as in a nurses' station or in the room of a patient) and/or remotely from the medical facility (such as a care provider's mobile device). Additionally, the server system 102 may be located locally at or remotely from the medical facility.

When reviewing diagnosis record 104 via a machine-human interface, such as a display or audio interface of a care provider device, a care provider may enter an input (e.g., via the user input device, which may include a keyboard, mouse, microphone, touch screen, stylus, or other device) that may be processed by the care provider device and sent to the server system 102. In examples where the user input is a selection of a link or user interface control button of a user interface of the diagnosis record, the user input may trigger display of different user interfaces or display states of the diagnosis record, each of which may present outputs of the algorithms in different formats with varying amount of information, as described further below.

The server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, diagnostic test results, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, ECGs, as well as microphones, cameras, continuous blood pressure bracelets, and other devices. The monitoring devices 120 may send output directly to the server system 102 and/or may send output to the EMR database 122. For example, a plurality of monitoring devices monitoring patient 1 may be configured to send output to the server system 102 which may then store and analyzed the received outputs. The server system 102 may then communicate the analyzed data or reports based on the analyzed data to a care provider device (care provider device 134).

The hospital operational systems 118 may direct creation of and control access to each diagnosis record. For example, when a patient is admitted, the hospital operational systems 118 may associate the patient with an identifier (e.g., an identification code) and push a notification of a newly admitted patient to the server system 102. In alternate embodiments, the server system 102 may periodically query the hospital operation systems 118 to identify newly admitted patients. After the server system 102 receives a signal indicating and/or determines based on queried information that a new patient has been admitted, the server system 102 may proceed to generate a diagnosis record for that patient, as described further below.

After a care provider sees a patient and inputs health data, the care provider, via the care provider device 1, for example, may initiate the creation of an updated diagnosis record 104 based on outputs of the plurality of algorithms run on the digital twin 108. In still other embodiments, the created diagnosis record may continuously update as new patient health data is received by the server system 102.

Server system 102 may further store instructions for (e.g., in memory 130) and be configured to execute (e.g., via processor(s) 132) a plurality of data acquiring modules and algorithms 135. The data acquiring modules may acquire patient health data, standards and guidelines, and historical and demographic data (pertaining to the patient, to other patients, or data derived from the historical data, as described further below) from external sources. The algorithms 135 may then use the acquired data, compiled as and into the digital twin, to generate the diagnosis record 104. The algorithms 135 may be part of a unique module, or may be part of the data acquiring modules described below. As shown, the server system 102 includes an electronic medical record (EMR) module 110, a standards/guidelines module 112, a historical and demographic data module 114, a non-medical sensor module 116, and a monitoring module 117. The modules may be realized as several modules, each for a different purpose, various groups of modules, or as one overall module, which represents all the different external data gathered and used by the algorithms 135 for generating the diagnosis record 104.

EMR module 110 is configured to retrieve and/or receive patient information from an electronic medical record database, such as EMR database 122. This retrieved patient information may then be used by the processor 132 to generate the digital twin 108 of the patient. EMR database 122 may be an external database accessible by EMR module 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR software is configured to control access to patient electronic medical records such that only authorized healthcare providers may edit and access the electronic medical records. An EMR for a patient may include patient demographic information, family medical history, past medical history, preexisting medical conditions, current medications, allergies, surgical history, past medical screenings and procedures, past hospitalizations and visits, etc. Thus, the EMR module 110 serves as a connection to the EMR database. The EMR module may also update the EMR database for a patient based on the generated digital twin 108 and diagnosis record 104 of the patient.

Guideline module 112 is configured to retrieve relevant care guidelines from an external guideline service 124. Guideline module 112 may retrieve different care guidelines based on the different algorithms being run and/or based on outputs of the algorithms. For example, based on one or more diagnoses predicted based on outputs of the plurality of algorithms 135, the processor(s) 132 may request for the guideline module 112 to retrieve guidelines for those particular diagnoses and then use the algorithms outputs, as well as the guidelines, to generate the information in the diagnosis record. In another example, the algorithms may use the retrieved care guidelines from the guideline module 112 as additional inputs into the algorithms for generating the diagnosis record 104 and may request particular care guidelines from the guideline module 112 during running of one or more of the plurality of algorithms. In one embodiment, the guideline module 112 may search an a priori index of available guideline data to retrieve the relevant care guidelines. In another embodiment, via the guideline module, a search may be performed of the guideline data for relevant references, guidelines, standards, and the like.

For example, different algorithms may predict an onset or presence of a different medical condition (e.g., sepsis, diabetes, acute kidney injury, and the like) and if outputs of the algorithms indicate a particular diagnosis is possible, the guideline module may automatically retrieve standards and guidelines (e.g., treatment guidelines, additional indications for the disease state, and the like) for the particular diagnosis. The algorithms 135 may then use the retrieved standards and guidelines to present (e.g., display or communicate via audio device) relevant guidelines to the care provider and/or generate recommendations or next actions (e.g., diagnostic tests to run on the patient), based on the diagnoses identified by the caregiver through normal human insight and request, or by the mechanisms of the plurality of algorithms 135, as part of the diagnosis record 104.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the server system 102 services. Further, external guideline service 124 may include differential diagnoses trees that guideline module 112 may access to determine potential diagnoses based on a patient condition or state via the algorithms 135.

For example, the guideline module 112 may enter specific search terms to the guideline service 124 based on patient state and symptoms (e.g., SOFA score of five, glucose level of 190 mg/dL), or the guideline module 112 may specifically ask for guidelines for a given condition (e.g., sepsis), based on the specific algorithms being run and/or based on diagnoses output via the plurality of algorithms 135.

Historical and demographic data module 114 is configured to retrieve historical and/or demographic medical data pertaining to different patient populations and medical conditions from an external historical and demographic data service 126, which may be similar to the external guideline service 124 described above, but contain historical and/or demographic medical data categorized by patient population and medical condition. The historical and/or demographic medical data may also include data derived from the historical data, such as parameters of a machine-learned model. External historical and demographic data service 126 may be a remote service accessed via a network, or external historical and demographic data service 126 may be a local service executed on a computing device of the hospital. As one example, based on the digital twin 108 generated for the patient, the historical and demographic module 114 may retrieve historical records (including actual outcomes) of other patients (e.g., previous patients) whose digital twin matches, or is closest to, the current patient's digital twin. The algorithms 135 may then use this retrieved historical data to generate recommendations, next actions (for narrowing down a diagnosis, for example), present similar patients to the healthcare provider, and/or indicated diagnoses for the diagnosis record 104.

Non-medical sensor module 116 is configured to receive outputs from non-medical sensors 121 and may track a patient condition or state based on the received outputs. In other embodiments, the non-medical sensor module 116 is configured to receive outputs from the non-medical sensors 121 (also referred to as surveillance devices) and transfer the received outputs to the processor(s) 132 to generate the digital twin 108. In this way, the processor 132 may retrieve the received outputs from the non-medical sensors and use them in generating the digital twin 108. The non-medical sensors may include various cameras, microphones, and non-medical grade sensing devices (such as a continuous blood pressure bracelet), attached to or in the vicinity of (e.g., in the same room as) the patient.

Monitoring module 117 is configured to receive outputs from the medical sensors and devices of the monitoring devices 120 and may track a patient condition or state based on the received outputs. The processor 132 may retrieve the received outputs from the medical sensors and devices and use them in generating the digital twin 108.

The modules described above (e.g., modules 110, 112, 14, 116, and/or 117) may work in conjunction with the algorithms 135 and the generation of the digital twin 108 via processor(s) 132. For example, the modules may be configured to process medical information of the patient (e.g., vital signs, medical history, current symptoms) received from the patient EMR, the monitoring devices, the care providers, and/or other sources and then transfer this information to the processor(s) 132 for the generation the digital twin 108 of the patient. The modules may be further configured to retrieve specific data used by the algorithms 135 in generation of the diagnosis record 104. Further, the modules and/or algorithms may include one or more machine learning algorithms that are trained using optimization methods. In some embodiments, one or more trained, machine learning algorithms may be trained using medical terminology data. In this way, the modules may be accessed by a similar module configured to execute the algorithms 135 and/or the modules may be part of or be combined into a single module that is adapted to run the algorithms 135. Further description of the algorithms 135 are described below with reference to FIG. 2

Server system 102 includes a communication module 128, memory 130, and processor(s) 132 to store and execute the digital twins, diagnosis records, algorithms, and modules, as well as send and receive communications, graphical user interfaces, audio communications or interfaces, medical data, and other information.

Communication module 128 facilitates transmission of electronic data within and/or among one or more systems. Communication via communication module 128 can be implemented using one or more protocols. Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 includes one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. In certain examples, users (e.g., a patient and/or care provider) can access functionality provided by server system 102 over a cloud or other computer network, for example. In certain examples, all or part of server system 102 can also be provided via a platform as a service (SaaS or PaaS), infrastructure as a service (IaaS), etc. For example, server system 102 can be implemented as a cloud-delivered Mobile Computing Integration Platform as a Service. A set of consumer-facing Web-based, mobile, and/or other applications enable users to interact with the PaaS, for example. Further, while server system 102 is shown in FIG. 1 as constituting a single entity, it is to be understood that server system 102 may be distributed across multiple devices, such as across multiple servers.

While not specifically shown in FIG. 1, additional devices described herein (care provider device 134, care provider device 136, and care provider device 138, hospital operational systems 118, monitoring devices 120, EMR database 122, external guideline service 124, external historical and demographic service 126) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. User input devices for the care provider devices may include keyboards, mice, touch screens, microphones, or other suitable devices.

As used herein, the computing device of system 100 may include one or more of server system 102 and the care provider devices (e.g., the processor and display and/or audio interface of a care provider device). For example, as explained further below with reference to FIG. 2, the server system 102 may output a graphical user interface for display on a display device, which may include a display screen of a care provider device (e.g., smart phone, smart watch, smart speaker, table, laptop computer, and/or desktop computer). In other embodiments, the server system 102 may output an audio file for communication to a user via an audio interface (e.g., microphone) of the care provider device. The graphical user interfaces and/or audio interfaces may have different forms, as described further below, and present data in different formats from the diagnosis record 104.

FIG. 2 shows an example schematic 200 of an implementation of the healthcare provider assistance system 100 of FIG. 1. Specifically, schematic 200 shows a flow of data and information, from the different sources described above with reference to system 100, into the plurality of algorithms 135, and the outputs from the algorithms 135. Schematic 200 shows a digital twin 108 and diagnosis record 104 for a single example patient. However, as described above, server system 102 may have a unique digital twin 108 and diagnosis record 104 for each patient being seen at a hospital, clinic, or medical facility.

Schematic 200 shows various data inputs into the digital twin 108, including EMR data 210, monitoring device data 217, diagnostic data 218, and non-medical sensor data 216. Though four data inputs are shown in FIG. 2, it should be noted that, in alternate embodiments, additional data sources relating to the health of the patient may also be present and used to generate the digital twin 108 of the patient. The EMR data 210 may be obtained from the EMR module 110 and/or EMR database 122 shown in FIG. 1, and may include past and current medical data for the patient, including health conditions, health statistics (weight, height, age, sex, nationality, or the like), past diagnostic test results, medications, family history, and the like. Monitoring device data 217 may include data processed by the monitoring module 117 and/or received directly from the monitoring devices 120, and may include real-time data from pulse oximeters, heart rate monitors, blood glucose monitors, ECGs, and the like, which may be attached to the patient in the medical facility. In this way, the monitoring device data 217 may be continuously received at the server system (e.g., at monitoring module 117) and continuously input into the digital twin 108. As described further below, the digital twin 108 may be continuously updated as input data is received and/or updated. Diagnostic data 218 may include data and/or test results from medical imaging procedures, lab tests (such as blood and urine tests), and the like and may be obtained from the monitoring devices 120 and/or monitoring module 117. Non-medical sensor data 216 may be obtained from the non-medical sensor module 116 and/or monitoring devices 120, and may include data output from non-medical sensors such as cameras, microphones, and non-medical grade sensing devices (such as a continuous blood pressure bracelet), attached to or in the vicinity of (e.g., in the same room as) the patient.

The digital twin 108 is a digital representation of the health of the patient. The digital twin 108 may be generated by the processor(s) of the server system (e.g., processor(s) 132) and/or one/or more modules of the server system, according to instructions, models, and/or algorithms stored in memory of the system and using the data inputs described above. The resulting digital twin 108 may be a digital compilation of all available health data on the patient and may be continuously updated, in real-time, as data is received by the processor(s) of the system, to reflect the current health of the patient. The digital twin 108 may represent all the data a medical professional (e.g., healthcare provider) would use to perform a differential diagnosis of the patient's medical condition.

The digital twin 108 is stored on the server system (e.g., in memory) and is used as an (electronic) input into the algorithms 135. Algorithms 135 include a plurality of different algorithms, such as a first algorithm 220, second algorithm 222, third algorithm 224, fourth algorithm 226, and fifth algorithm 228. Though five algorithms are shown in FIG. 2, more or less than five algorithms may be included in algorithms 135. For example, the plurality of different algorithms 135 may include at least two algorithms, more than three algorithms, ten algorithms, 50 algorithms, 100 algorithms, or the like. The algorithms 135 may be diverse in function, but may all output information relevant to the patient and their health condition and treatment. In one embodiment, each of the algorithms 135 may predict the presence of a different medical condition in the patient. For example, first algorithm 220 may be adapted to (according to the specific code of the algorithm) predict sepsis in the patient based on the input to the algorithms, second algorithm 222 may be adapted to (according the specific code of the algorithm) predict diabetes in the patient based on the input to the algorithms, third algorithm 224 may be adapted to (according to the specific code of the algorithm) predict acute kidney injury in the patient based on the inputs to the algorithm, fourth algorithm 226 may be adapted to (according to the specific code of the algorithm) predict myocardial infarction in the patient based on the input to the algorithms, and fifth algorithm 228 may be adapted to (according to the specific code of the algorithm) predict hyperthyroidism in the patient based on the input to the algorithms. As shown in in FIG. 2, each of algorithms 135 uses the same input which includes the same digital twin 108, and each of the algorithms 135 are run in parallel with one another. However, each of algorithms 135 may output different information for the medical provider, such as a different possible disease state, a confidence metric (e.g., percentage confidence) of the presence of a certain disease state, treatment guidelines for the disease state or diagnosis, and/or next actions for narrowing down or confirming the output diagnosis or diagnoses. Additionally, in some embodiments, while the same digital twin 108 is used by and input into each of algorithms 135, each algorithm 135 may use all or only a subset of all the data within the digital twin 108. For example, each of algorithms 135 may be configured to pull and use a specific subset of the available data in the digital twin for running the specific algorithm.

Algorithms 135 may be configured to run in complementary, competitive, or aggregated modes. In the complementary mode, each of the algorithms 135 looks for different implications of the status of the digital twin 108. For example, first algorithm 220 may look at indications of infection and, second algorithm 222 may look at heart performance, and third algorithm 224 may look for signs of pulmonary distress. The outputs from each of the complementary run algorithms may be used to formulate the diagnosis report and be presented to a user and/or an additional algorithm (such as a meta algorithm) may use the outputs from the complementary algorithms to determine a list of possible diagnoses. In the competitive mode, algorithms 135 (each different in their structure or approach) may offer different perspectives based on the same digital twin 108. For example, each of algorithms 135 may indicate the likelihood of the presence of a different disease state in the patient. In the case of any given patient condition, one could get a "majority report" and a "minority report" of the status of the patient based on the diversity of algorithmic results. For example, the majority report may include the most prevalent diagnosis (or diagnoses, e.g., the top 3 most frequently occurring or output diagnoses from the plurality of algorithms 135) predicted by the plurality of algorithms 135 while the minority report may include the least prevalent diagnosis (or diagnoses) predicted by the plurality of algorithms 135. In the aggregated mode, a supervisory algorithm takes the outputs of all of the parallel running algorithms 135 and creates a composite or aggregated result that is published and presented to the caregiver. For example, the supervisory algorithm may include code adapted to take the outputs of each of algorithms 220, 222, 224, 226, and 228 (which may include a different diagnosis and/or disease indications, in one example) and formulate a differential diagnosis of the patient, including a list of possible diagnoses of the patient.

In another embodiment, algorithms 135 may additionally or alternatively include one or more algorithms (e.g., one or more of algorithms 220, 222, 224, 226, and 228) that include code adapted to, based on the input digital twin 108, stratify the risk of the patient to deteriorate within a set time window. In this embodiment, the one or more algorithms may output a probability (e.g., percentage) of the likelihood of the patient to deteriorate within a predetermined time window.

Each of algorithms 135 may utilize additional information, which may be considered additional inputs, and may include historical and demographic data 214 (obtained from historical module 114 and/or external historical and demographic data service 126 in FIG. 1) and medical standards/guidelines 212 (obtained from guideline module 112 and external guideline service 124). In some embodiments, each algorithm may request/pull relevant historical and/or demographic data from the historical module 114 and relevant standards/guidelines from the guideline module 124. For example, if first algorithm 220 is adapted to predict sepsis in the patient, first algorithm 220 may utilize historical and/or demographic data and/or standards/guidelines specific to sepsis.

The outputs from each of algorithms 135 may be stored within a diagnosis record 104 for the patient. For example, the output of each algorithm may be stored in the diagnosis record 104 and/or the results from running parallel algorithms in the complementary, competitive, or aggregated modes may be stored in the diagnosis record 104. Further, a majority or minority report of the outputs of algorithms 135 may be formulated at the diagnosis record 104, by the processor(s) of the server system, and/or by another one of algorithms 135 and then stored in the diagnosis record 104. The processor(s) may perform a meta-analysis, via a meta algorithm in one example, on the results of each of the algorithms 135, and store the results of the meta-analysis in the diagnosis record 104. The meta-analysis results may include a differential diagnosis of the patient, including a finite list of most likely, possible diagnoses (e.g., a list of two, three, four, five, or the like, diagnoses) based on the outputs of the algorithms 135. In this way, the diagnosis record 104 may include the outputs (e.g., results) from each of the algorithms 135 run in parallel, on the same digital twin 108, and one or more aggregated or summary analyses of the algorithm outputs. In some embodiments, the diagnosis report 104 may include medical standards/guidelines data 212 related to the resulting diagnoses in the diagnosis report 104 (received from the guidelines module 112, for example). In another embodiment, the diagnosis report 104 may include historical data 214 (including actual outcomes) of other patients whose digital twin matches, or most closely matches, the current patients' digital twin 108 (as received/pulled from the historical module 114, for example). Additionally, the diagnosis record may present the percentage likelihood of a plurality of possible diagnoses output by the algorithms and/or a percentage likelihood of a diagnosis, which may have been from an output list, as confirmed by a healthcare provider. Additionally, the diagnosis record may summarize the patient's health status, which may become part of the healthcare provider's notes on the patient and/or medical record.

Additionally, the diagnosis record 104 may be adapted based on the healthcare provider's preferences and/or interaction with the system (e.g., diagnosis record of server system 102) via a care provider device (such as care provider device 134 shown in FIG. 1). For example, if the physician relies on or selects a diagnosis or result output from a particular algorithm more frequently than other algorithms, or takes actionable results based on the diagnosis output from the particular algorithm (such as listing that diagnosis in the medical record of the patient, ordering diagnostic tests or labs to confirm the particular diagnosis, or the like), the system may mark (e.g., tag) the particular algorithm as "more trusted" and, as a result, prioritize the results/outputs from that algorithm over the other algorithms for future updates to the diagnosis record 104 and/or for alternate diagnosis records of different patients (seen by the same healthcare provider). In this way, the system (e.g., server system 102) may include machine learning capabilities for learning algorithm preferences of a certain healthcare provider. The machine learning capabilities may be stored as programmable code, as instructions, in memory of the processor(s) described above with reference to FIG. 1. This prioritization by the system shown in FIGS. 1 and 2 may be performed over a unique provider-patient interaction or as a statistical measure of algorithm usefulness over an ensemble of interactions, within the same medical ward, facility, or even globally.

Additionally, algorithms 135 may include a plurality of algorithms, each of which may be run each time the digital twin 108 is updated. In an alternate embodiment, only a subset of the plurality of algorithms 135 (e.g., three out of the five shown in FIG. 2) may be run on the digital twin 108 of the patient. For example, the machine learning of the server system may select a subset of, or all of, the plurality of algorithms 135 based on the digital twin 108 and/or based on learned user preferences, as explained above. In one example, only a subset of the algorithms 135 may be run on the digital twin 108 if one or more of the algorithms 135 does not apply to the patient (e.g., one of algorithms 135 is configured to predict a condition only present in babies and the patient is an adult). Thus, prior to executing the algorithms 135, the system may first select the relevant algorithms from algorithms 135 and then execute the selected algorithms 135 on the digital twin 108. The relevant algorithms may be further prompted or selected based on user input (e.g., the healthcare provider requests that a certain disease state is screened for via the algorithms).

Results of the diagnosis record 104 are then presented to a user (e.g., medical professional, such as a nurse, physician, or physician's assistant) via a machine-human interface 208. In one embodiment, the machine-human interface 208 may be a display including a display screen of a display device, such as one of care provider devices 134, 134, and 138 shown in FIG. 1. In another embodiment, the machine-human interface 208 may be an audio interface included on one of care provider devices 134, 134, and 138 shown in FIG. 1. Different user interfaces may be presented to a user, via the machine-human interface 208, based on stored user preferences, one or more selections at the machine-human interface 208 via the user, and/or based on a preset order of presentation of the user interfaces. FIG. 2 shows three user interfaces, including user interface 202, user interface 204, and user interface 206. However, in alternate embodiments, more or less than three user interfaces may be available for presentation to the user. In one embodiment, the user interfaces may be audio interfaces presented to the user through a speaker or similar audio device. In another embodiment, the user interfaces may be user interface displays (e.g., graphical user interfaces) which may be displayed via a display of a user device. Example user interface displays are shown in FIGS. 3-8, as described further below.

In one embodiment, each user interface display may be a graphical user interface that includes a visualization of all, a portion of, or a summary of, the algorithm results in the diagnosis record 104. As one example, user interface display 202 may include a visualization of first list of a plurality of possible diagnoses of the patient based on outputs of the plurality of different algorithms that were run on the digital twin 108. User interface display 204 may include a visualization of a summary/majority report including the majority diagnosis. User interface display 206 may include a visualization of details on an algorithm and/or diagnosis, which may be selectable from one of the other user interface displays (such as user interface display 202). In this way, different user interface displays may present different information to the medical professional which may be used to more quickly, easily, and accurately diagnose a condition of the patient and take actionable steps (e.g., treatments, further tests, and the like). In alternate embodiments, the user interface displays described above may be audio interfaces that present, in an audible format, the summary or specific portions of the algorithm results.

FIGS. 3-8 show examples of different user interface displays (e.g., graphical user interfaces) that may be displayed to a medical professional (e.g., nurse, physician, or the like) via a display device (e.g., an iPad, smart phone, laptop computer, desktop computer, and the like) 308. Specifically, each of FIGS. 3-8 show a different example user interface display. As explained further below, the different user interfaces displays of FIGS. 3-8 may be linked to one another via one or more selectable buttons displayed on the various user interface displays. The different user interface displays may also be automatically displayed to the user, after a user selects the diagnosis record for a patient, based on settings previously selected by the user. For example, the care provider may select a patient, out of a plurality of patients they are seeing, from a menu user interface display (not shown). After selecting the patient, the user may request, via another user interface display, to see the diagnosis record 104 of the selected patient. The care provider device (e.g., display device 308) may then automatically display one or more of the user interface displays shown in FIGS. 3-8, as described further below. In one example, user interface display 300 shown in FIG. 3 may be the default user interface display that is displayed on the display device 308 when the care provider selects the diagnosis record of a specific patient. However, in alternate embodiments, another one of the user interface displays described herein may be set as the default user interface display which is automatically displayed after selection of the diagnosis record of the specific patient. In yet another embodiment, a diagnosis record menu with links to each of the user interface displays described below may be automatically displayed upon selection of the diagnosis record of the specific patient. All of the information displayed visually via the user interface displays, as described below, is part of the diagnosis record 104 for the patient, as determined based on outputs of the plurality of different algorithms run on the digital twin of the patient. Each of the user interface displays described below may include a home button 302 which returns the care provider to the diagnosis record menu or a main menu for the selected patient and an exit button 304 which may exit the diagnosis record application for the patient and close out of the system completely. However, in alternate embodiments, these home and exit buttons may not be present, only one of these buttons may be present, or an alternate menu button that returns the user to an alternate menu user interface display may be included.

Figure 3:
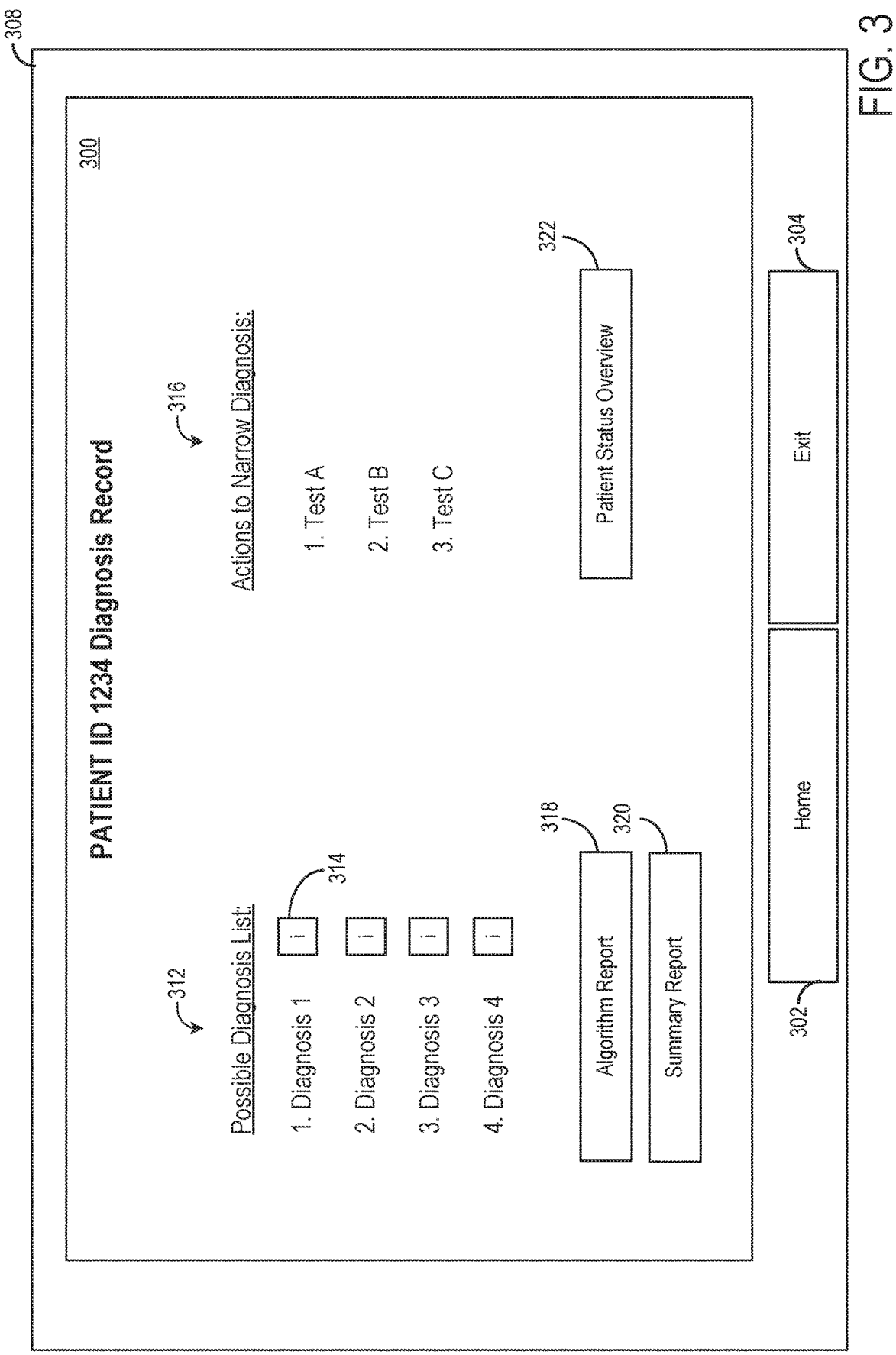
FIG. 3 shows a first example user interface display for a differential diagnosis list view for a diagnosis record of a patient.

Turning first to FIG. 3, user interface display 300 is a diagnosis list view (also referred to herein as a differential diagnosis summary) for the diagnosis record of the patient (e.g., patient ID 1234). User interface display 300 includes a visualization of a list of possible diagnoses 312 of the patient, as determined based on outputs of the plurality of different algorithms. As shown in FIG. 3, the list of possible diagnoses includes a list of four different diagnoses. However, in alternate embodiments, the list may include more or less than four different diagnoses (depending on the outputs of the algorithms). The list of possible diagnoses 312 may be similar to a differential diagnosis of the patient, as performed automatically by the algorithms using the digital twin of the patient as the input. An information button 314 is included next to each of the diagnoses listed in the list of possible diagnoses 312. The information button 314 may be selectable via a user (e.g., via a user input such as a finger or stylus touch to the screen of the display device 308, or via another user input device such as a mouse or keyboard) to display a corresponding user interface display which may be a detailed diagnosis summary page that includes additional details (e.g., which data points of the digital twin contributed to each of the suggested diagnoses) on the selected possible diagnosis. In an alternate embodiment, the listed possible diagnosis itself (e.g., "Diagnosis 1") may be selectable to display the corresponding detailed diagnosis summary page user interface display.

Figure 4:
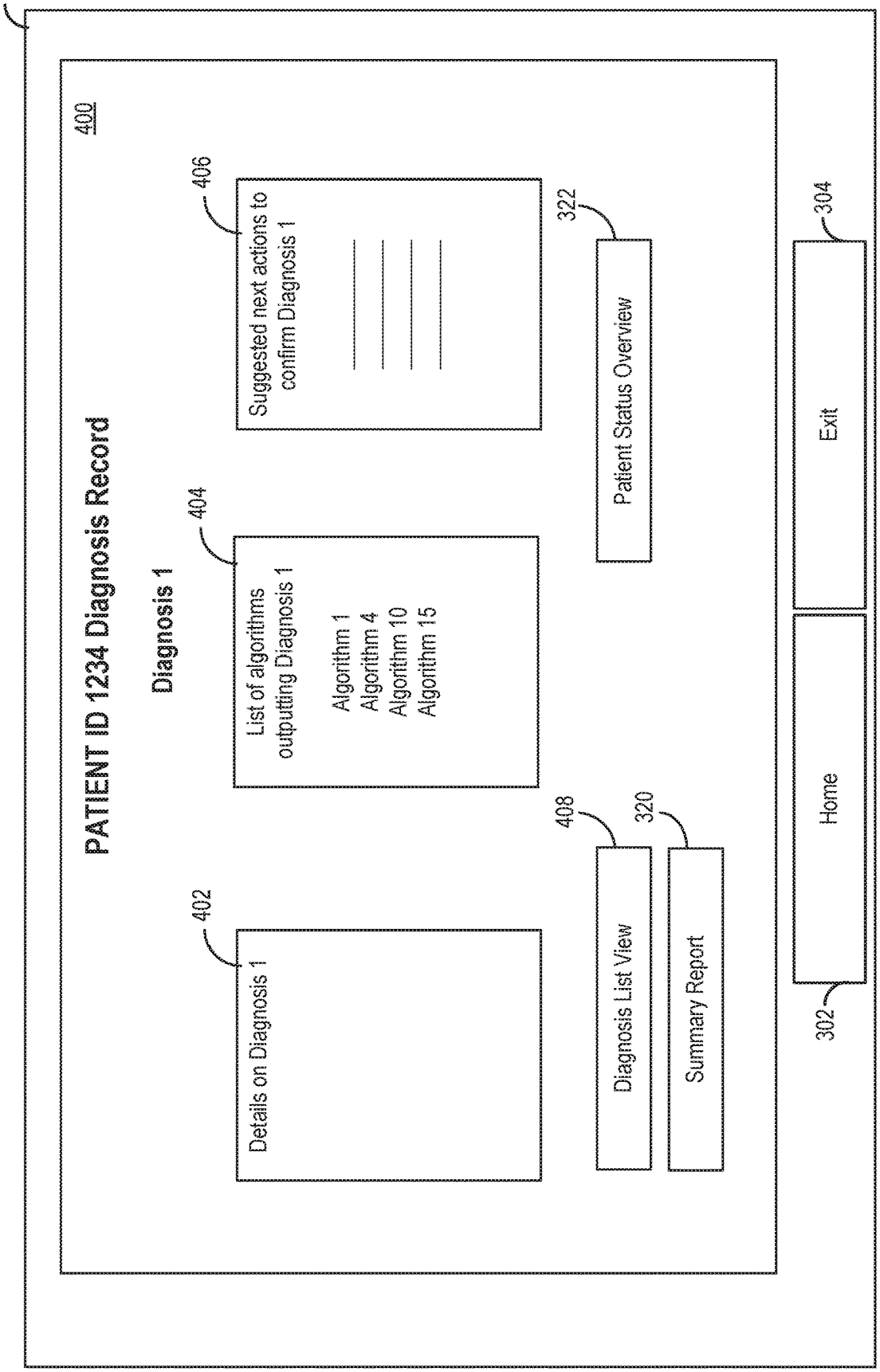
FIG. 4 shows a second example user interface display for a detailed diagnosis summary page for a diagnosis record of a patient.

An example user interface display 400 showing a detailed diagnosis summary page, reachable via selection of the information button 314 next to the desired diagnosis or via selection of the listed diagnosis itself (e.g., "Diagnosis 1" in possible diagnosis list 312 of user interface 300) is shown in FIG. 4. For example, after a user selects information button 314 next to Diagnosis 1 on user interface display 300, user interface 400 may be automatically displayed via display device 308. User interface display 400 includes (e.g., a visualization of) details on the selected diagnosis at 402. The details on the selected diagnosis 402 may include a text summary or list of details on the selected diagnosis, historical/demographic data on the selected diagnosis, treatment guidelines for the selected diagnosis, and/or the like. The user interface display 400 may also include a visualization of a list of algorithms that output or determined the selected diagnosis at 404. Each of the algorithms listed at 404 may be individually selectable to display a detailed algorithm report for the selected algorithm. For example, selection of "Algorithm 1" may automatically result in the display, via display device 308, of a detailed algorithm report for Algorithm 1, as described further below with reference to FIG. 7. The user interface display 400 may also include a visualization of suggested next actions to confirm the selected diagnosis at 406. The suggested next actions may include one or more diagnostic tests to run, such a blood tests, urine tests, imaging procedures (e.g., ultrasound, Mill, x-ray, and the like), and the like. User interface display 400 may further include a plurality of buttons to return or navigate to other, related user interface displays, such as diagnosis list view button 408 which results in the display of user interface display 300 of FIG. 3, summary report button 320 which results in the display of user interface display 500 of FIG. 5 (as described further below), and patient status overview button 322 which results in the display of user interface display 800 of FIG. 8 (as described further below). In alternate embodiments, different or additional buttons for navigating to different, related user interface displays of the diagnosis record of the patient may be included in user interface display 400 and the other user interface displays described herein.

Returning to FIG. 3, user interface display 300 may additionally include a visualization of actions to narrow down the diagnosis of the patient at 316. For example, the actions to narrow down the diagnosis 316 may include one or more suggested diagnostic tests (e.g., labs, imaging procedures, and the like) to run on the patient in order to narrow down the list of possible diagnoses at 312. For example, following one or more of the actions at 316 to obtain additional health data on the patient may result in narrowing the list of diagnoses at 314 from four to two diagnoses. The actions listed at 316 may be generated based on the outputs of the algorithms, the resulting diagnoses in the diagnosis list 312, and/or based on medical standards and guidelines (e.g., standards and guidelines data 212 in FIG. 2). For example, based on the possible diagnoses listed at 312, as determined from outputs of the algorithms, the system (e.g., the systems shown in FIGS. 1 and 2) may determine additional diagnostic tests that may narrow down the diagnosis, according to medical standards and guidelines for the listed diagnoses. For example, Test A, listed at 316 may be used to rule out on or more of the diagnoses listed at 312. In some examples, the actions to narrow down the diagnosis 316 may include additional instructions, such as if the result of Test A is X, you should perform Test B to further narrow the possible diagnosis list 312, or, if the result of Test A is Y, you should perform Test B to further narrow the possible diagnosis list 312. In this way, user interface display 300 may provide instructions to the user (e.g., care provider) on how to narrow the diagnosis of the patient in the most efficient manner possible. As explained further below, upon receiving test results from one or more of the tests listed at 316, the system (e.g., server system 102) may automatically update the digital twin of the patient, re-run the algorithms on the updated digital twin, and update the displayed user interface display 300. The updated user interface display 300 may include a smaller number of diagnoses in the possible diagnosis list 312 (e.g., there may only be two diagnoses listed, such as Diagnosis 1 and Diagnosis 2). The user interface display 300 may then be updated with a new set of actions to narrow the diagnosis at 316.

User interface display 300 may additionally include a plurality of buttons to return or navigate to other, related user interface displays, such as Algorithm Report button 319 which is selectable to display user interface 600 of FIG. 6 (as described further below), Summary Report button 320 which is selectable to display user interface display 500 of FIG. 5 (as described further below), and Patient Status Overview button 322 which is selectable to display user interface display 800 of FIG. 8 (as described further below).

Figure 5:
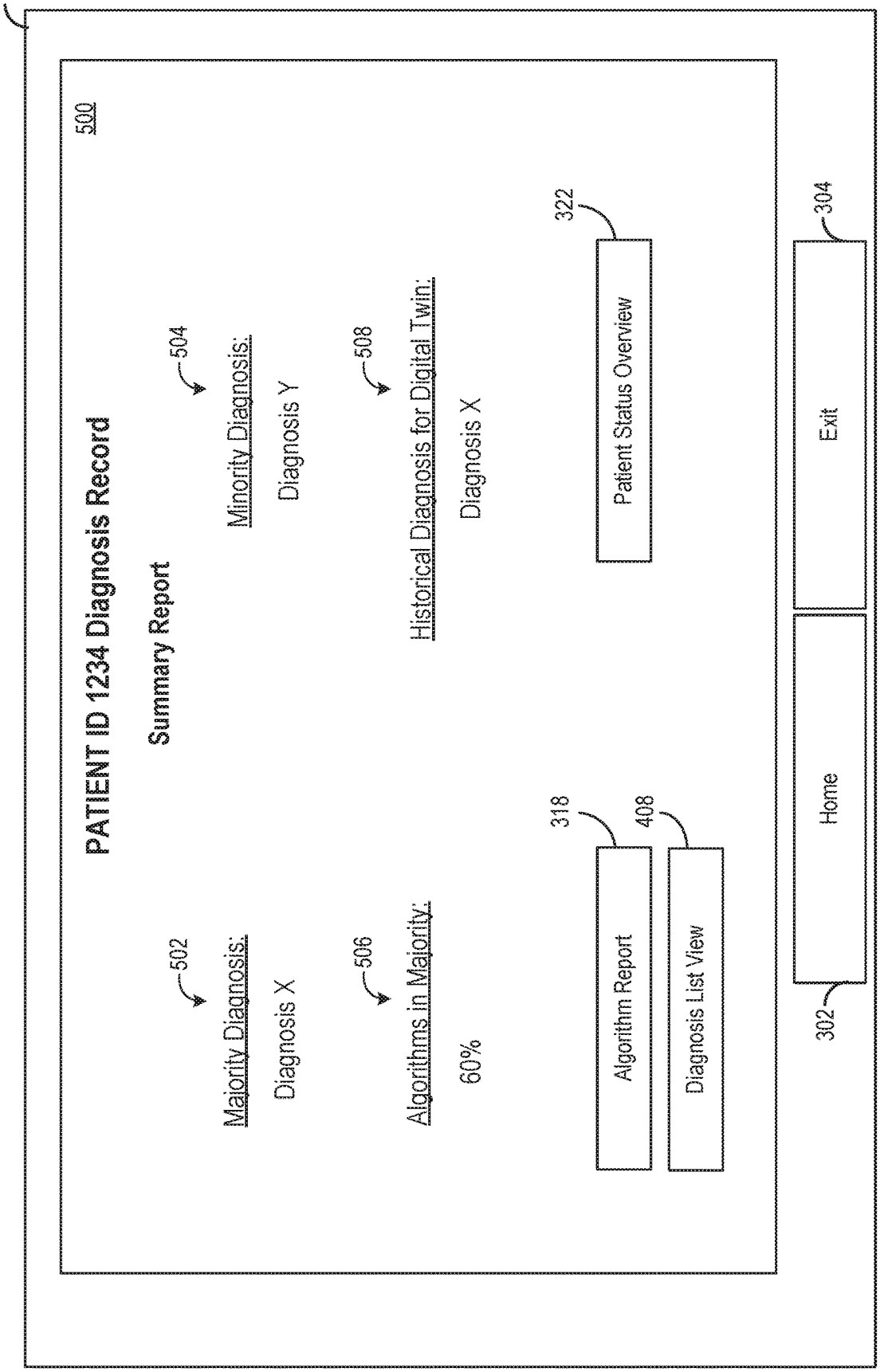
FIG. 5 shows a third example user interface display for a summary report view for a diagnosis record of a patient.

Turning to FIG. 5, user interface display 500 is a summary report view which presents a summary or majority report of the algorithm results to the user. Specifically, in the example shown in FIG. 5, user interface display 500 includes a visualization of a majority diagnosis at 502. The majority diagnosis 502 may list the most prevalent diagnosis (e.g., Diagnosis X) output by the algorithms. The listed majority diagnosis at 502, "Diagnosis X", may be selectable by the user to automatically switch to display, via display device 308, a user interface display of a detailed diagnosis record, such as user interface display 400 of FIG. 4. User interface display 500 may also include a visualization of a percentage of the algorithms that output or predicted the majority diagnosis 502, at 506. The percentage (e.g., 60%) displayed at 506 may be selectable by the user to automatically switch to a display of a user interface display of an algorithm report, such as the user interface 600 of FIG. 6 (as described further below). The algorithm report may list the different algorithms that output and/or predicted the presence of the majority diagnosis. In some embodiments, as shown in FIG. 5, user interface display 500 may additionally include a visualization of a minority diagnosis at 504 which includes a listing of the least prevalent diagnosis (e.g., Diagnosis Y) output by the algorithms. The listed minority diagnosis at 504, "Diagnosis Y", may be selectable by the user to automatically switch to display, via display device 308, a user interface display of a detailed diagnosis record for Diagnosis Y, such as user interface display 400 of FIG. 4. In alternate embodiments, user interface display may not include the visualization of the minority diagnosis 504. In some embodiments, as shown in FIG. 5, user interface display 500 may additionally include a visualization of a historical diagnosis based on the digital twin of the patient at 508. The historical diagnosis listed at 508 (Diagnosis X in this example) may be output by an algorithm configured to determine, based on historical and/or demographic data, a diagnosis of a previous patient having a health history (e.g., health record) most like the digital twin of the current patient. In this way, the user may be presented with a historical diagnosis of a patient having similar health data to the current patient. User interface display 500 may include similar navigation buttons (Algorithm Report button 318, Diagnosis List View button 408, and Patient Status Overview button 322) as described above for the previously presented user interface displays.

Figure 6:
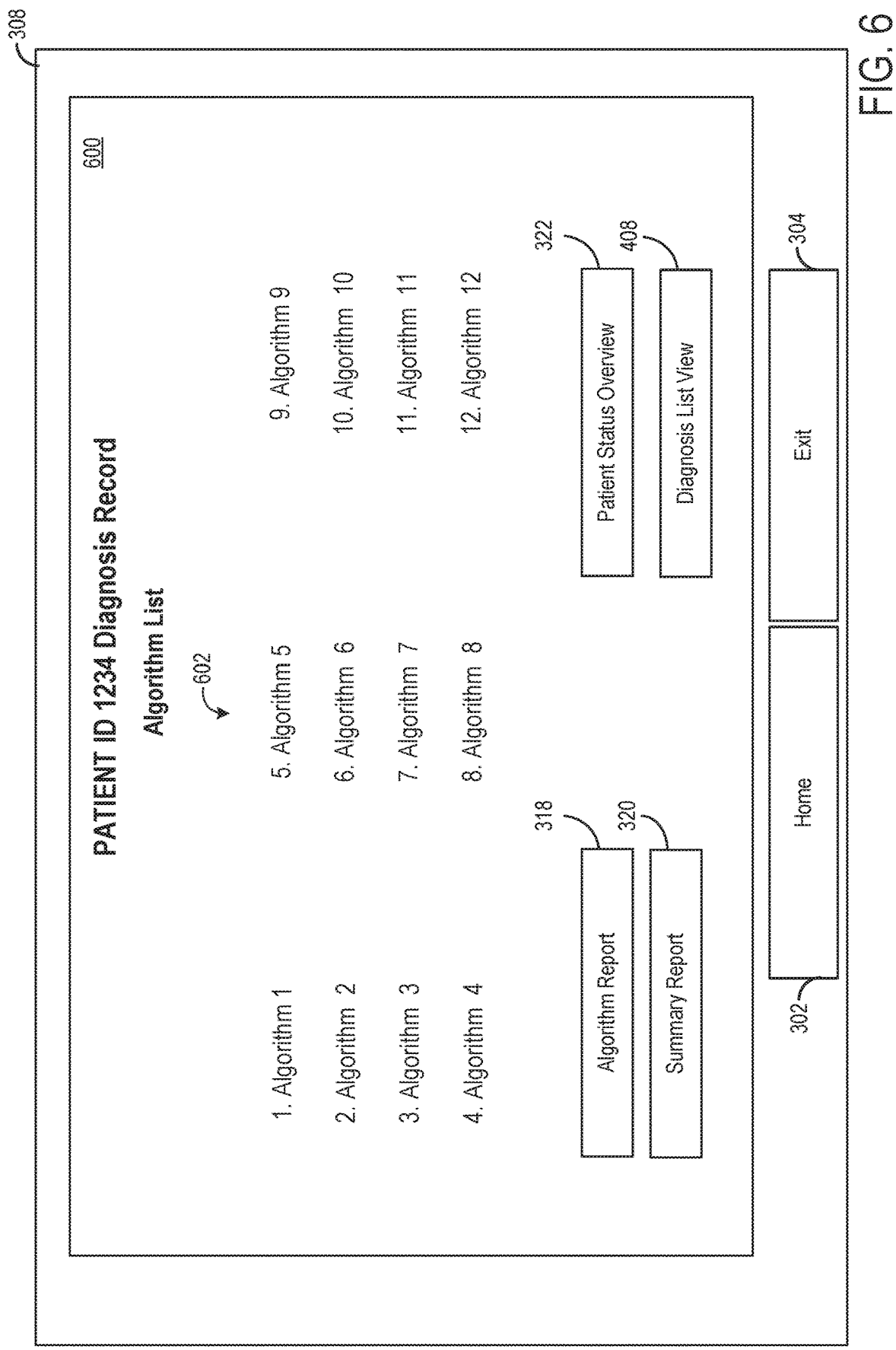
FIG. 6 shows a fourth example user interface display for an algorithm report for a diagnosis record of a patient.

Continuing to FIG. 6, user interface display 600 is an algorithm report which presents all of the different algorithms run on the digital twin of the patient, the different algorithms that output the diagnoses listed in the possible diagnosis list of the diagnosis list view (in FIG. 3), and/or the different algorithms that output and/or predicted the presence of the majority diagnosis listed in the summary report (in FIG. 5). Specifically, user interface display 600 includes a visualization of a list of algorithms at 602. Each algorithm listed at 602 may be individually selectable, via the screen of the display device 308, to automatically display a corresponding, detailed algorithm report, such as user interface display 700 shown in FIG. 7 (as described further below). In some embodiments, user interface display 600 may include additional statistics on the plurality of algorithms that were run on the digital twin of the patient, such as a percentage of algorithms outputting a certain diagnosis (such as the majority diagnosis) and/or the most trusted algorithm (as learned by the system and/or set by the user). User interface display 600 may include similar navigation buttons (Algorithm Report button 318, Summary Report button 320, Diagnosis List View button 408, and Patient Status Overview button 322) as described above for the previously presented user interface displays.

Figure 7:
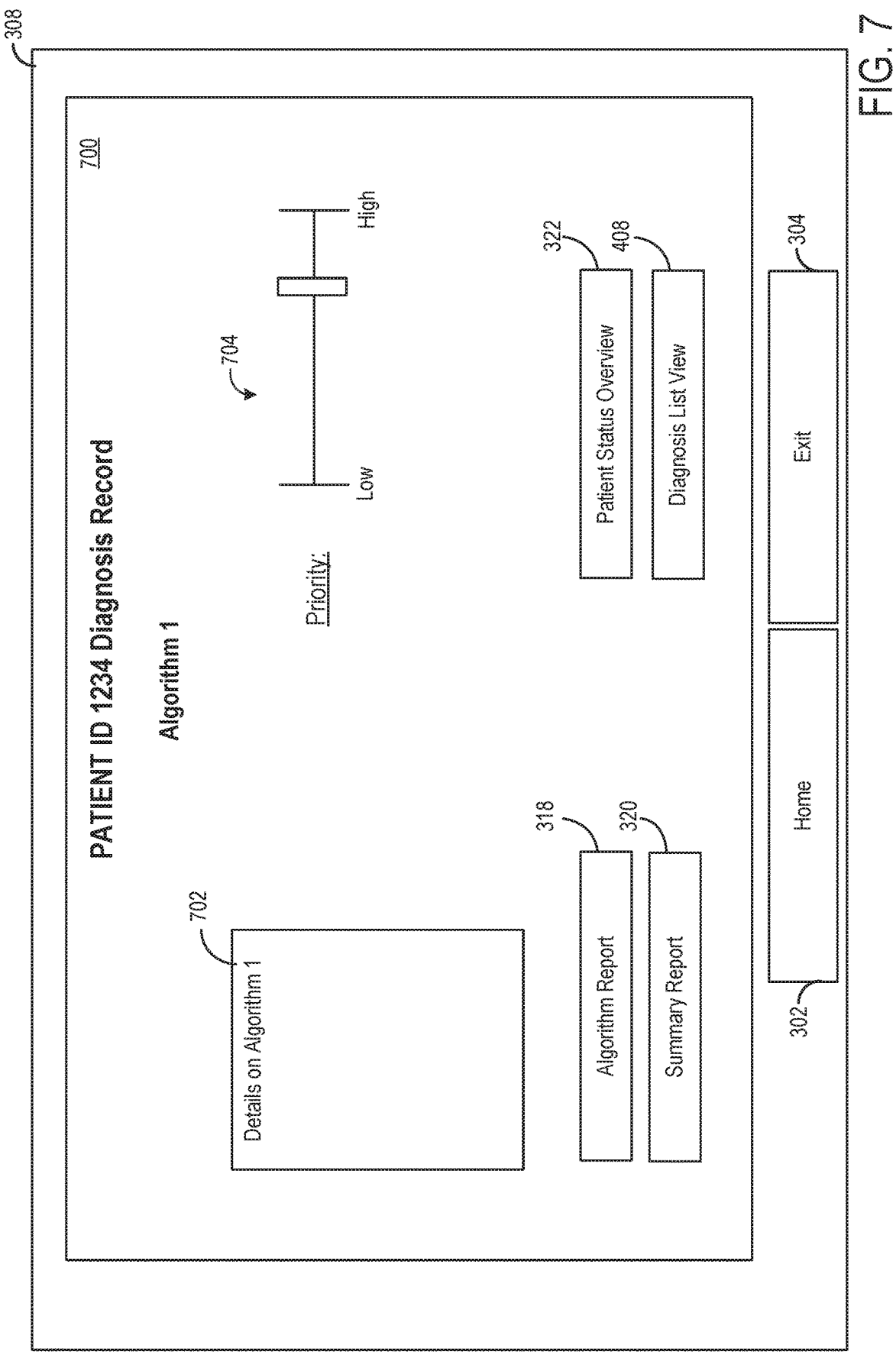
FIG. 7 shows a fifth example user interface display for a detailed algorithm report for a diagnosis record of a patient.

FIG. 7 shows user interface display 700 which includes a detailed algorithm report presenting additional details of a (selected) algorithm run on the digital twin and that output results to the diagnosis record. User interface display 700 may be reachable from and automatically displayed in response to a corresponding button or selection of a specific algorithm listed on another user interface display, such as one of the user interface displays described above (e.g., user interface display 600, user interface display 500, and/or user interface display 400). User interface display 700 shows an example detailed algorithm report for Algorithm 1. User interface display 700 may include a visualization of details on the selected algorithm at 702. The details on the selected algorithm 702 may include a text summary or list of details on the selected algorithm, including what disease state or biological system it is configured to detect and/or monitor, historical usage data on the selected algorithm, specifics on the code and/or configuration of the selected algorithm, and/or the like. User interface display 700 may additionally include a visualization of a set priority of the selected algorithm at 704. As explained above, the system may learn a priority of a particular algorithm and/or a user may set and/or adjust the priority of the selected algorithm. For example, the higher the priority, the more the output of the selected algorithm is emphasized over outputs of other algorithms, and thus, it may carry more weight in determining the differential diagnosis list and/or majority diagnosis. As shown at 704, the user, via the display device 308, may set the priority of the selected algorithm. As shown in the example of user interface display 700, the visualization of the priority setting is a slide-bar movable between a relatively low and high setting. However, in alternate embodiments, the visualization of the priority setting at 704 may be a different type of visualization, such as an adjustable percentage, a vertical movable bar, or the like. User interface display 700 may include similar navigation buttons (Algorithm Report button 318, Summary Report button 320, Diagnosis List View button 408, and Patient Status Overview button 322) as described above for the previously presented user interface displays.

Figure 8:
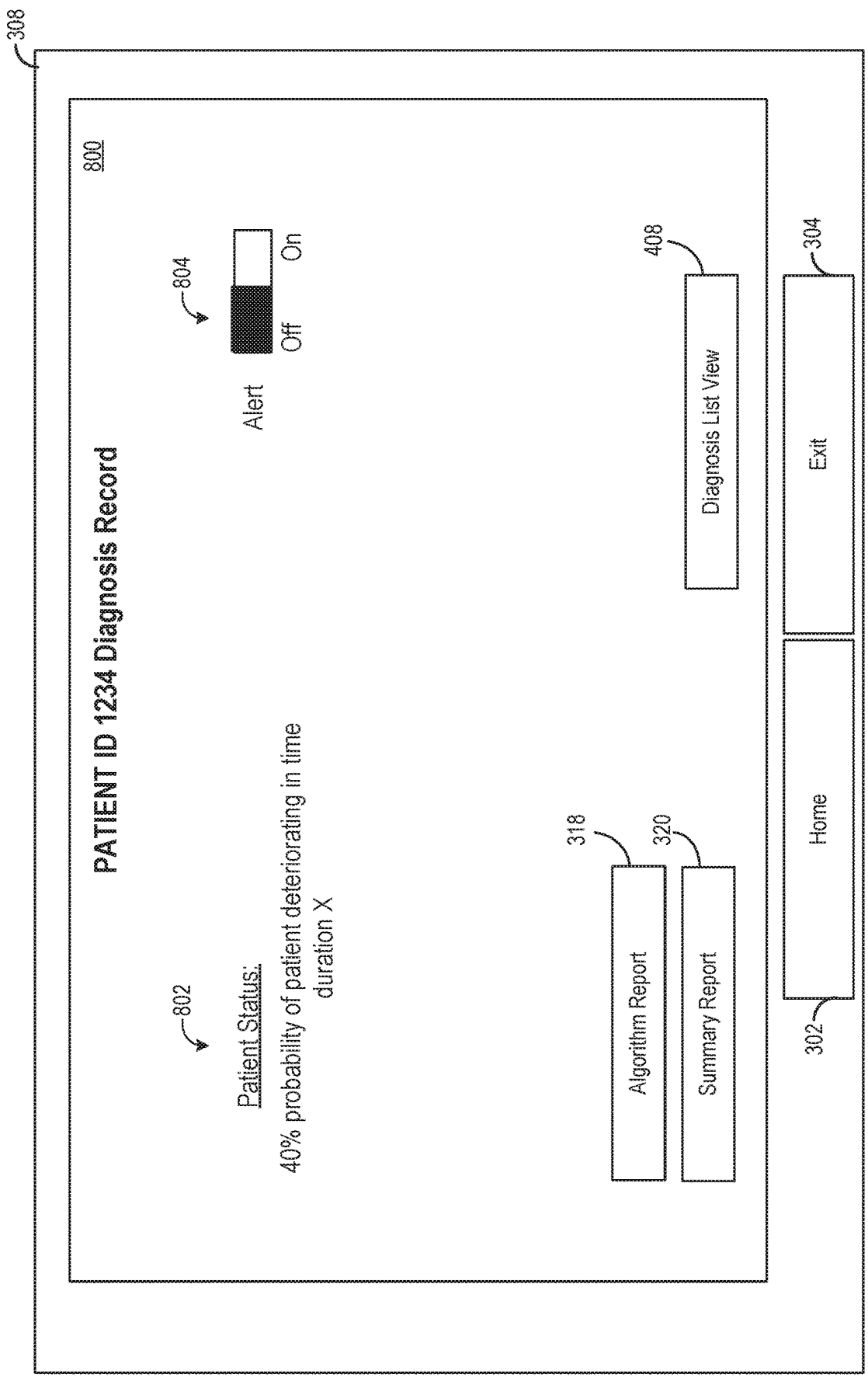
FIG. 8 shows a sixth example user interface display for a patient status report for a diagnosis record of a patient.

Turning to FIG. 8, user interface display 800 is displayed via display device 308. User interface display 800 is a patient status report which depicts a health status of the patient. For example, user interface display 800 may display a patient status at 802 which includes a probability (e.g., percentage) of the likelihood of the patient to deteriorate within a predetermined time window (e.g., duration X). In another embodiment, the visualization of the patient status at 802 may include a relative text scale (e.g., unstable/moderately stable/very stable) or color scale (e.g., red, yellow, green). User interface display 800 may also include a visualization of an alert status at 804. For example, a user may set an alert to on or off, where when the alert is "on" the system may automatically alert (via a pop-up dialog box, flashing indicator light, audible noise, or the like) when the patient status crosses a threshold level (e.g., probability at 802 increases above 70%).

It should be noted that the user interface displays presented in FIGS. 3-8 are exemplary in nature and may include alternate or additional visualizations for providing assistance to the health care provider based on outputs of a plurality of different algorithms run on the same digital twin of the patient. The user interface displays may provide an organized and instructive visualization of the diagnosis record of the patient and enable a health care provider to more quickly and accurately perform a differential diagnosis on the patient. For example, one or more of the user interface displays may provide the user, via one or more user inputs (such as buttons or displayed, selectable elements, as described above, or via audio inputs), the ability to specify the final selected diagnosis. A report, similar to one or more of the reports described herein, may then me generated and/or the final, selected diagnosis may be used for future machine learning tasks that may then be implemented for future differential diagnoses using the system described herein.

Figure 9:
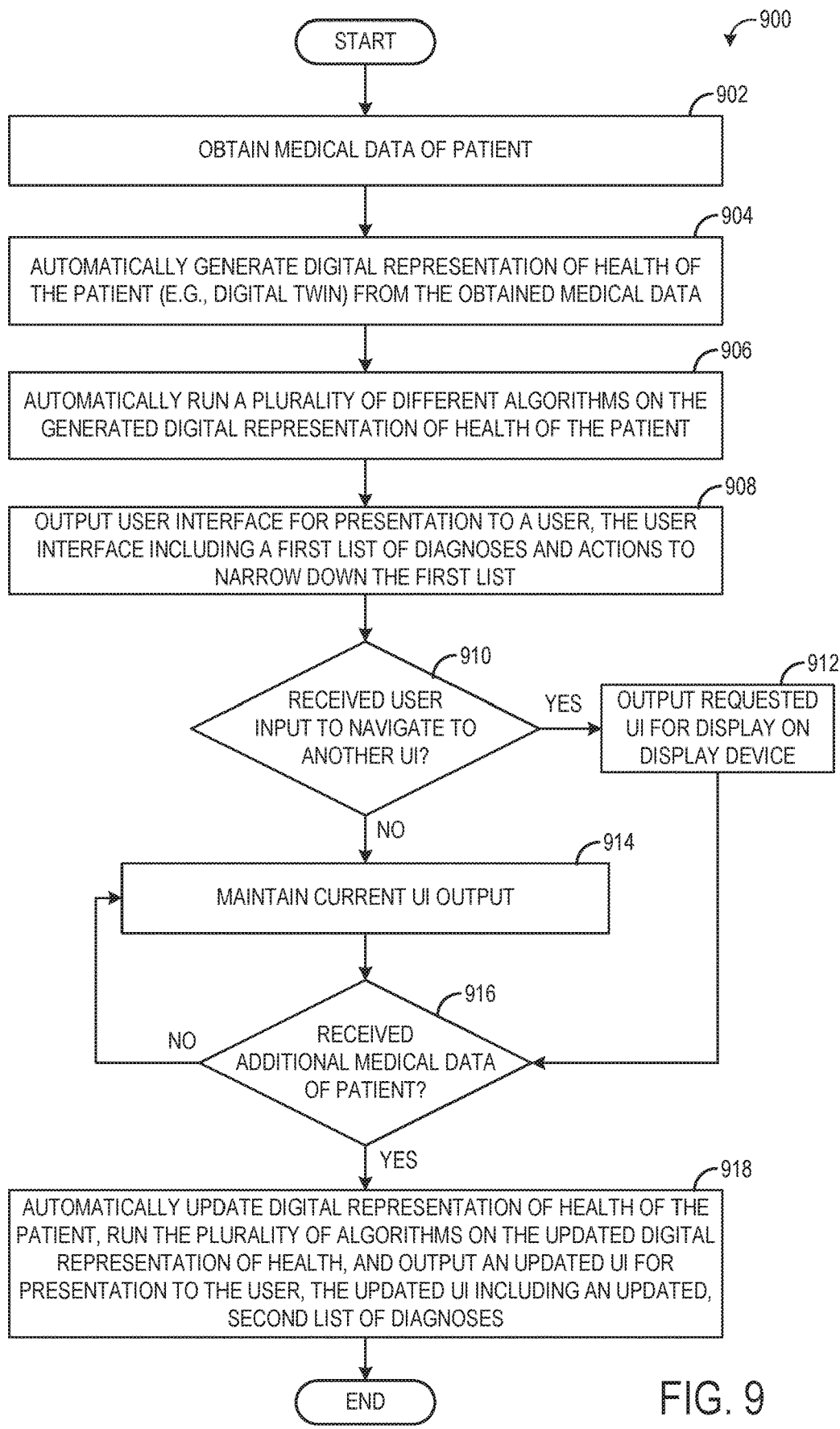
FIG. 9 shows a flow chart illustrating an example method for providing assistance to a healthcare provider in diagnosing and caring for a patient.

FIG. 9 shows a flow chart of a method 900 for providing assistance to a healthcare provider in diagnosing and caring for a patient. Method 900 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the healthcare provider assistance system (e.g., patient medical data signals from monitoring devices 120, communication from hospital operational systems 118, communication from a care provider device, etc.) and signals sent from the server system to the care provider devices and/or other system components. The processor(s) executing method 900 may additionally include one or more modules of the server system, such as one or more of the modules shown in FIG. 1.

At 902, method 900 includes obtaining medical data of a patient. Obtaining medical data of the patient may include obtaining past (e.g., historical or previously obtained medical data on the patient, such as from an EMR system or database, as described herein) and present (e.g., current data obtained in real-time from one or more patient monitoring devices or via inputs from a user) medical data of the patient. As described above with reference to FIGS. 1 and 2, the medical data of the patient may include EMR data (e.g., EMR data 210 in FIG. 2), monitoring device data (e.g., monitoring device data 217 in FIG. 2), diagnostic data (e.g., diagnostic data 218 shown in FIG. 2), and non-medical sensor data (e.g., non-med sensor data 216 shown in FIG. 2). This data may be obtained (e.g., received at the processor(s)) in real-time (e.g., from monitoring devices and non-medical sensors), received via user inputs (e.g., manual data input from a care provider device and/or from the hospital operational system in communication with the processor(s)), and/or obtained (e.g., pulled from or received from) external databases such as an EMR database (e.g., EMR database 122 shown in FIG. 1). In this way, obtaining medical data may include acquiring (and receiving the required data) data with a medical device coupled to or in proximity to the patient and passively pulling previously acquired medical data from a separate medical device, database, or the like. For example, previous imaging procedure data may be pulled from an EMR database, hospital operational system, and/or historical database.

The method continues to 904 to automatically generate a digital representation of health of the patient from the obtained medical data. The digital representation of health of the patient may be referred to herein as the digital twin of the patient (such as the digital twin 108 of FIGS. 1 and 2, as described above). The processor(s) of the system may compile all the medical data obtained at 902 to generate the digital representation of the patient and store the digital representation in memory of the computing device. As explained further herein, the processor(s) may be configured to automatically update the digital twin of the patient in response to receiving new and/or updated health data on the patient. For example, if new imaging or lab results are uploaded to the system, the processor(s) may then automatically update the digital twin based on the newly received data.

At 906, method 900 includes automatically running a plurality of different algorithms on the generated digital representation of health of the patient, where all or subset of the data from the same generated digital representation of health of the patient is input into each of the plurality of different algorithms. The plurality of algorithms (e.g., algorithms 135 shown in FIGS. 1 and 2, as described above) may be part of and run by the processor(s) of the device and include code configured to output diagnosis data related to the patient. For example, the digital twin of the patient may be input into each algorithm that is selected to run (e.g., all stored algorithms or a subset of all the stored algorithms which are selected based on user input, learned user preference, and/or based on the digital twin itself, as described above) and then the executed algorithms may output one or more or a plurality of possible diagnoses of the patient. In this way, the outputs of the algorithms are based on the input digital twin of the patient. Further details on the algorithms are described above with reference to FIG. 2. For example, as described above, each of the plurality of different algorithms is adapted to identify a different diagnosis using the generated digital representation of the patient as an input.

At 908, the method includes outputting a first user interface for presentation to a user, the user interface including a first list of diagnoses and actions to narrow down the list. In one example, the user interface is an audio or graphical user interface. For example, the first (graphical) user interface may be displayed on a display device, the first graphical user interface including a visualization of a first list of a plurality of possible diagnoses of the patient based on outputs of the plurality of different algorithms and a visualization of suggested next actions to narrow down the first list of the plurality of possible diagnoses, the suggested next actions based on outputs of one or more of the automatically run plurality of different algorithms. In one example, the first graphical user interface may be similar to user interface display 300 shown in FIG. 3. As one example, the first graphical user interface may be output for display on the display device in response to a user (e.g., care provider) selecting the patient, selecting the diagnosis report of the patient, and/or selecting the differential diagnosis summary listing (e.g., diagnosis list view) of the diagnosis report of the patient from one or more menu displays output for display on the display device and presented to the user. In some embodiments, a care provider may receive an alert (audible or visual) via their care provider device, indicating that the diagnosis record of the patient has been updated (e.g., the plurality of algorithms have been automatically run on an updated digital twin of the patient) and is ready to be viewed by the care provider. Additionally, the suggested next actions may include one or more diagnostic tests to perform on the patient. For example, the suggested next actions may include one or more imaging procedures to execute (e.g., x-ray, ultrasound, MRI, or the like) and/or lab tests (e.g., blood test, urine test, and the like) to run on the patient. The suggested next actions may additionally or alternatively include certain values or results to obtain and input from the executed diagnostic tests. In one embodiment, the suggested next actions may include an ordered list of actions to take to narrow down the diagnosis. For example, the ordered list of next actions may include executing a first diagnostic test and then, based on those results, either executing a second or third diagnostic test. The ordered list of next actions may additionally or alternatively include a list of diagnostic tests to perform in a specified order.

At 906, method 900 includes determining whether the system has received user input to navigate to another user interface. For example, the first user interface may display one or more navigation buttons that are individually selectable by the user to display another user interface display, or the diagnoses and/or actions in their respective lists presented on the first graphical user interface may be individually selectable to display another user interface display related to the selected element. For example, as described above, selecting one of the listed diagnoses may cause the system to automatically display a user interface display of a detailed diagnosis summary including additional details on the selected diagnosis. In this way, receiving the user input may include receiving a signal from the display device of the care provider device that the user has selected one of the buttons or features displayed at the first graphical user interface. In response to receiving such a signal, the method proceeds to 912 to output the requested (e.g., a second) graphical user interface (e.g., user interface display) for display on the display device. Further details on examples of linked user interface displays are described above with reference to FIGS. 3-8.

If the method determines the system has not received a user input requesting to navigate to another user interface, the method proceeds to 914 to maintain the current user interface output. This may include continuing to display the first graphical user interface on the display device. Alternatively, this may include presenting the same audio user interface to the user via the user device.

At 916, method 900 includes determining whether additional medical data of the patient has been received. For example, executing one or more of the suggested next actions may include in the system receiving test results or additional health data on the patient in real-time via patient monitoring devices and/or the hospital operation systems (e.g., lab or diagnostic data updated to an operational system of the hospital/clinic/office). In this way, the additional medical data may include results from one or more diagnostic test. If no additional medical data of the patient (e.g., different from the original data used to generate the digital twin of the patient) is received, the method returns to 914. Alternately, if additional medical data is received at the device (e.g., system), the method proceeds to 918 to automatically update the generated digital representation of health of the patient (e.g., digital twin) based on the received additional medical data, automatically run the plurality of different algorithms on the updated digital representation of health of the patient, and output an updated first user interface for display on the display device (or for presenting via the audio interface), the updated first user interface including a visualization (or audio representation) of an updated, second list of a plurality of possible diagnoses of the patient based on outputs of the plurality of different algorithms. For example, the second list may include different and/or fewer diagnoses than the first list. In this way, the additionally received medical data may help to narrow the differential diagnosis presented to the user to a smaller number. In some example, the second list may have more diagnoses than the first list, but second list may contain more accurate diagnosis, therefore enabling a user to more accurately diagnose the patient and implement an effective treatment plan. The method then ends. In some embodiments, the method may return to 904 and repeat.

In one embodiment, method 900 may repeat until the differential diagnosis list is narrowed enough such that the care provider may make an accurate diagnosis of the patient. The system, via the diagnosis record, may additionally present the user with actions (e.g., treatments) to take based on a selected or finalized diagnosis of the patient.

In this way, the healthcare provider assistance system described above may provide a healthcare provider assistance in diagnosing a patient. By compiling all available health data on the patient via a digital twin, a plurality of algorithms may then be executed on the same digital twin. Integrating the patient medical data in this way may save the healthcare provider a considerable amount of time and effort, thereby allowing them to focus their time and effort on higher level clinical tasks. Outputs from the plurality of algorithms may be used to form a diagnosis record of the patient which may include digital information regarding possible diagnoses of the patient, the patient health status, additional actions to take to confirm and/or narrow the possible diagnoses, suggested treatments based on the possible diagnoses, and/or the like. This information may then be presented to a user (healthcare provider) in various forms, via user interface displays and/or audible user interfaces. The user may interact with the user interface display or audible user interface to navigate through the different information from the diagnosis record. In this way, the system may present information on the patient in an organized manner that enables the provider to quickly and effectively narrow down a diagnosis of the patient and accurately treat the patient. The system described above, including the algorithms, mimics the thought process that the healthcare provider would go through to diagnose a patient. However, the system performs this process in a more thorough, organized, and efficient manner and with increased accuracy. Thus, the technical effect of automatically running a plurality of different algorithms on a generated digital representation of health of the patient, where the same generated digital representation of health of the patient is input into each of the plurality of different algorithms; and outputting a graphical user interface for display on a display device, the first graphical user interface including a visualization of a first list of a plurality of possible diagnoses of the patient based on outputs of the plurality of different algorithms and a visualization of suggested next actions to narrow down the first list of the plurality of possible diagnoses, the suggested next actions based on outputs of one or more of the automatically run plurality of different algorithms, is providing organized information pertaining to the heath of the patient to a healthcare provider and enabling them to make a more accurate diagnosis of the patient in a more timely and easy manner (as compared to performing a traditional differential diagnosis from an EMR and from memory and/or looking up standards and guidelines).

As one embodiment, a system, comprises: a machine-human interface; and a computing device operably coupled to the machine-human interface and configured to execute instructions stored in memory to: execute a plurality of different algorithms where inputs to each of the plurality of different algorithms include current and past data representing a health and current condition of a patient, where each of the plurality of different algorithms uses the same data, or a subset of the same data, for the inputs; output, to the machine-human interface, a list of a first number of possible diagnoses of the patient based on outputs of the executed plurality of different algorithms; and present, via the machine-human interface, suggested next actions to narrow down the first number of possible diagnoses, the suggested next actions determined based on the outputs of the executed plurality of different algorithms. In a first example of the system, the instructions are further executable to receive additional patient health data obtained from execution of the suggested next actions and output to the machine-human interface an updated list of a second number of possible diagnoses, the second number less than the first number. A second example of the system optionally includes the first example and further includes, wherein the instructions are further executable to output to the machine-human interface an updated list of a second number of possible diagnoses in response to receiving additional patient health data, where the updated listed includes different diagnoses than the list of the first number of possible diagnoses and wherein the first number and second number may be the same or different. A third example of the system optionally includes one or more of the first and second examples, and further includes, wherein the presented suggested next actions includes an ordered list of diagnostic tests to perform on the patient. A fourth example of the system optionally includes one or more of the first through third examples, and further includes wherein the instructions further include instructions to output to the machine-human interface a majority report indicating a most likely diagnosis of the patient based on a most frequently occurring output of the plurality of different algorithms. A fifth example of the system optionally includes one or more of the first through fourth examples, and further includes wherein inputs to each of the plurality of different algorithms further includes demographic data and medical standards and guidelines data and wherein the past data includes health data of the patient from an electronic health record of the patient and wherein the current data includes real-time patient monitoring data. A sixth example of the system optionally includes one or more of the first through fifth examples, and further includes wherein each of the plurality of different algorithms is adapted to identify a different disease based on the inputs. A seventh example of the system optionally includes one or more of the first through sixth examples, and further includes wherein the machine-human interface is a display of a care provider device, wherein the computing device includes one or more processors, and wherein the computing device is in electronic communication with one or more databases or services, directly or indirectly through an additional server, the one or more databases or services including an electronic medical record database, an external guideline service, and an historical and demographic data service.

As another embodiment, a method, comprises: obtaining medical data of a patient; automatically generating a digital representation of health of the patient from the obtained medical data; running a plurality of different algorithms on the generated digital representation of health of the patient, where the same generated digital representation of health of the patient is input into each of the plurality of different algorithms; and outputting a first graphical user interface for display on a display device, the first graphical user interface including a visualization of a first list of a plurality of possible diagnoses of the patient based on outputs of the plurality of different algorithms and a visualization of suggested next actions to narrow down the first list of the plurality of possible diagnoses, the suggested next actions based on outputs of one or more of the automatically run plurality of different algorithms. In a first example of the method, the suggested next actions include one or more diagnostic tests to perform on the patient. A second example of the method optionally includes the first example and further includes receiving additional medical data of the patient, the additional medial data including results from the one or more diagnostic tests and/or updated medical data of the patient; automatically updating the generated digital representation of health of the patient based on the received additional medical data; automatically running the plurality of different algorithms on the updated digital representation of health of the patient; and outputting an updated first graphical user interface for display on the display device, the updated first graphical user interface including a visualization of an updated, second list of a plurality of possible diagnoses of the patient based on outputs of the plurality of different algorithms. A third example of the method optionally includes one or more of the first and second examples and further includes wherein the second list includes different and/or fewer diagnoses than the first list. A fourth example of the method optionally includes one or more of the first through third examples, and further includes wherein the obtained medical data includes current medical data of the patient and historical medical data of the patient. A fifth example of the method optionally includes one or more of the first through fourth examples, and further includes wherein each of the plurality of different algorithms is adapted to identify a different diagnosis using the generated digital representation of the patient as an input. A sixth example of the method optionally includes one or more of the first through fifth examples, and further includes wherein obtaining medical data of the patient includes acquiring data in real-time from a medical device adapted to monitor the patient and passively receiving data acquired by and stored at another medical device and/or data from a database. A seventh example of the method optionally includes one or more of the first through fourth examples, and further includes outputting a second graphical user interface for display on the display device in response to receiving a user input selecting a diagnosis of the visualization of the first list from the first graphical user interface, the second graphical user interface including a visualization of details on the selected diagnosis.

As yet another embodiment, a computing device, comprises: a machine-human interface, the computing device being configured to present via the machine-human interface a differential diagnosis summary listing one or more most likely possible diagnoses of a patient based on outputs of a plurality of different algorithms executed by the computing device, each algorithm of the plurality of different algorithms using a portion or all of a same set of current and past health data of the patient as inputs, where the one or more most likely possible diagnoses is selectable to present a corresponding detailed diagnosis summary including additional details on the selected possible diagnosis, where the details on the selected possible diagnosis includes suggested next steps to confirm the selected possible diagnosis. In a first example of the computing device, the suggested next steps include one or more diagnostic tests to run on the patient and wherein using the portion or all of the same set of current and past health data of the patient as inputs includes each algorithm selecting a portion of or all data included in the same set of current and past health data of the patient as inputs to the algorithm. A second example of the computing device optionally includes the first example and further includes, wherein the detailed diagnosis summary further includes a list of algorithms of the plurality of algorithms that output the selected possible diagnosis. A third example of the computing device optionally includes one or more of the first and second examples and further includes, wherein the machine-human interface is a display screen, wherein the differential diagnosis summary is included on a graphical user interface output to the display screen, and wherein the differential diagnosis summary further lists one or more suggested next actions to narrow down and/or confirm the one or more most likely possible diagnoses listed in the differential diagnosis summary.

In another representation, a system comprises: a display; and a computing device operably coupled to the display and configured to execute instructions stored in memory to: automatically generate a digital representation of health of a patient based on medical data of the patient; execute a plurality of different algorithms where inputs to each of the different algorithms includes the generated digital representation of health of the patient; output, to the display, a list of a first number of possible diagnoses of the patient based on outputs of the executed plurality of different algorithms; and continuously update the displayed list in response to receiving updates to the medical data of the patient. In one example, the instructions are further executable to obtain the medical data of the patient from an electronic medical health record of the patient, in real-time from data received from one or more patient monitoring sensors, and from received, uploaded diagnostic data including imaging and lab data for the patient.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a machine-human interface, wherein the machine-human interface is a display; and
a computing device operably coupled to the machine-human interface and configured to execute instructions stored in memory to:
execute a plurality of different algorithms where inputs to each of the plurality of different algorithms include current and past data representing a health and current condition of a patient, where each of the plurality of different algorithms uses the same data, or a subset of the same data, for the inputs;

output, via the machine-human interface, a differential diagnosis summary that includes a list of a first number of possible diagnoses of the patient determined based on outputs of the executed plurality of different algorithms;

present, via the machine-human interface, suggested next actions to narrow down the first number of possible diagnoses, the suggested next actions determined based on the outputs of the executed plurality of different algorithms; and responsive to receiving a selection of a diagnosis from the differential diagnosis summary at the machine-human interface, updating the display of the machine-human interface to present details of the diagnosis from the differential diagnosis summary, wherein the diagnosis is from the list of the first number of possible diagnoses of the differential diagnosis summary, and updating the display of the machine-human interface to present a list of algorithms that were used by the computing device to determine the diagnosis selected from the differential diagnosis summary.

2. The system of claim 1, wherein the instructions are further executable to receive additional patient health data obtained from execution of the suggested next actions and output to the machine-human interface an updated list of a second number of possible diagnoses, the second number less than the first number.

3. The system of claim 1, wherein the instructions are further executable to output to the machine-human interface an updated list of a second number of possible diagnoses in response to receiving additional patient health data, where the updated listed includes different diagnoses than the list of the first number of possible diagnoses and wherein the first number and second number may be the same or different.

4. The system of claim 1, wherein the presented suggested next actions to narrow down the first number of possible diagnoses includes an ordered list of diagnostic tests to perform on the patient, and wherein suggested next actions to confirm the diagnosis are further presented responsive to receiving the selection at the machine-human interface.

5. The system of claim 1, wherein the instructions further include instructions to output to the machine-human interface a summary report, the summary report including a majority diagnosis report indicating a most likely diagnosis of the patient based on a most frequently occurring output of the plurality of different algorithms and a minority diagnosis report.

6. The system of claim 1, wherein inputs to each of the plurality of different algorithms further includes demographic data and medical standards and guidelines data and wherein the past data includes health data of the patient from an electronic health record of the patient and wherein the current data includes real-time patient monitoring data.

7. The system of claim 1, wherein updating the display of the machine-human interface to present the list of algorithms used by the computing device to determine the diagnosis from the differential diagnosis summary is also responsive to receiving the selection at the machine-human interface.

8. The system of claim 1, wherein each of the algorithms presented in the list of algorithms are individually selectable to display a corresponding algorithm report.

9. A method, comprising:
obtaining medical data of a patient;
automatically generating a digital representation of health of the patient from the obtained medical data;

running a plurality of different algorithms on the generated digital representation of health of the patient automatically, where the same generated digital representation of health of the patient is input into each of the plurality of different algorithms;

outputting a first graphical user interface for display on a display device, the first graphical user interface including a visualization of a differential diagnosis summary that includes a first list of a plurality of possible diagnoses of the patient determined based on outputs of the plurality of different algorithms and a visualization of suggested next actions to narrow down the first list of the plurality of possible diagnoses, the suggested next actions to narrow down the first list of the plurality of possible diagnoses based on outputs of one or more of the automatically run plurality of different algorithms;

receiving a selection of a diagnosis from the differential diagnosis summary via the display device; and responsive to receiving the selection, presenting details of the diagnosis from the differential diagnosis summary via the display device, wherein the diagnosis is from the first list of the plurality of possible diagnoses, and presenting a list of algorithms that were used to determine the diagnosis selected from the differential diagnosis summary via the display device.

10. The method of claim 9, wherein the suggested next actions to narrow down the first list of the plurality of possible diagnoses include one or more diagnostic tests to perform on the patient, and wherein suggested next actions to confirm the diagnosis from the first list of the plurality of possible diagnoses are presented responsive to receiving the selection.

11. The method of claim 10, further comprising:
receiving additional medical data of the patient, the additional medical data including results from the one or more diagnostic tests and/or updated medical data of the patient;
automatically updating the generated digital representation of health of the patient based on the received additional medical data;
automatically running the plurality of different algorithms on the updated digital representation of health of the patient; and
outputting an updated first graphical user interface for display on the display device, the updated first graphical user interface including a visualization of an updated, second list of a plurality of possible diagnoses of the patient based on outputs of the plurality of different algorithms.

12. The method of claim 11, wherein the second list includes different and/or fewer diagnoses than the first list.

13. The method of claim 9, wherein the obtained medical data includes current medical data of the patient and historical medical data of the patient.

14. The method of claim 9, further comprising receiving selection of a summary report button displayed on the display device; and
presenting a summary report via the display device, the summary report including presentation of a majority diagnosis and a minority diagnosis responsive to receiving the selection of the summary report button, and
wherein each of the plurality of different algorithms is adapted to identify a different diagnosis using the generated digital representation of the patient as an input.

15. The method of claim 9, wherein obtaining medical data of the patient includes acquiring data in real-time from a medical device adapted to monitor the patient and passively receiving data acquired by and stored at another medical device and/or data from a database.

16. The method of claim 9, wherein the list of algorithms comprises a plurality of different algorithms that were used to determine the diagnosis.

17. A computing device, comprising:
a machine-human interface, wherein the machine-human interface is a display screen, the computing device being configured to present via the machine-human interface a differential diagnosis summary that includes a listing of one or more most likely possible diagnoses of a patient determined based on outputs of a plurality of different algorithms executed by the computing device, each algorithm of the plurality of different algorithms using a portion or all of a same set of current and past health data of the patient as inputs, where the one or more most likely possible diagnoses from the listing included in the differential diagnosis summary is selectable to present a corresponding detailed diagnosis summary via the display screen, where presenting the corresponding detailed diagnosis summary includes presenting additional details on a possible diagnosis selected from the differential diagnosis summary via the display screen, the possible diagnosis selected from the listing included in the differential diagnosis summary, and presenting a list of algorithms that were used by the computing device to determine the possible diagnosis selected from the differential diagnosis summary via the display screen, where the additional details on the possible diagnosis selected includes suggested next steps to confirm the possible diagnosis selected.

18. The computing device of claim 17, wherein the suggested next steps include one or more diagnostic tests to run on the patient and wherein using the portion or all of the same set of current and past health data of the patient as inputs includes each algorithm selecting a portion of or all data included in the same set of current and past health data of the patient as inputs to the algorithm.

19. The computing device of claim 17, wherein the differential diagnosis summary is included on a graphical user interface output to the display screen,
wherein the differential diagnosis summary further lists one or more suggested next actions to narrow down and/or confirm the one or more most likely possible diagnoses listed in the differential diagnosis summary.

20. The computing device of claim 17, wherein the list of algorithms comprises a plurality of different algorithms that were used by the computing device to determine the possible diagnosis.

\* \* \* \* \*